United States Patent [19]

Satoh et al.

[11] 4,169,051
[45] Sep. 25, 1979

[54] BLOOD PURIFICATION WITH COATED ACTIVATED CARBON SPHERES

[75] Inventors: Nagayasu Satoh, Machida; Hideo Takahira, Saitama; Kuniaki Terato, Tokyo, all of Japan

[73] Assignee: Eisai Co., Ltd., Tokyo, Japan

[21] Appl. No.: 849,960

[22] Filed: Nov. 9, 1977

Related U.S. Application Data

[63] Continuation of Ser. No. 698,607, Jun. 22, 1976, abandoned.

[30] Foreign Application Priority Data

Jun. 22, 1976 [JP] Japan ................. 51-698607

[51] Int. Cl.² .............. B01D 13/00; B01D 15/08
[52] U.S. Cl. .................... 210/23 R; 210/40; 252/426; 252/428
[58] Field of Search ............. 252/426, 428, 430; 210/22, 24 R, 36, 39, 40, 500 M, 502, 23 R; 427/2, 113, 221; 428/403

[56] References Cited

U.S. PATENT DOCUMENTS

| | | | |
|---|---|---|---|
| 2,794,584 | 6/1957 | Kunin | 210/24 |
| 3,442,819 | 5/1969 | Herbert | 210/36 |
| 3,775,344 | 11/1973 | Amagi | 210/40 |
| 3,891,574 | 6/1975 | Kobayashi | 210/40 |
| 3,901,808 | 8/1975 | Bokros | 210/DIG. 23 |
| 3,909,449 | 9/1975 | Nagai | 210/40 |
| 3,941,718 | 3/1976 | Barabas | 252/428 |
| 3,953,345 | 4/1976 | Saito | 210/40 |
| 3,953,360 | 4/1976 | Morishita | 210/39 |
| 3,972,818 | 8/1976 | Bokros | 210/DIG. 23 |
| 3,983,053 | 9/1976 | Courtney | 210/24 R |
| 3,991,018 | 11/1976 | Strup | 210/24 |
| 4,025,689 | 5/1977 | Kobayashi | 210/40 |
| 4,048,064 | 9/1977 | Clark | 210/500 M |
| 4,059,512 | 11/1977 | Harris | 210/24 |

FOREIGN PATENT DOCUMENTS 25117 of 1974 Japan.
18879 of 1975 Japan.

Primary Examiner—Thomas G. Wyse
Assistant Examiner—Ernest G. Therkorn
Attorney, Agent, or Firm—Wenderoth, Lind & Ponack

[57] ABSTRACT

A process to use coated beads-shaped activated carbon as an adsorbent in purification of the blood is disclosed. The absorbent is prepared by coating a beads-shaped activated carbon with a film-forming material. The coated beads-shaped activated carbon exhibits excellent properties with regard to the amount of the free carbon dusts, the ash to be dissolved out, the residual solvent, the degree of coagulation of the blood, and high safety, as compared with the conventional adsorbents.

5 Claims, 1 Drawing Figure

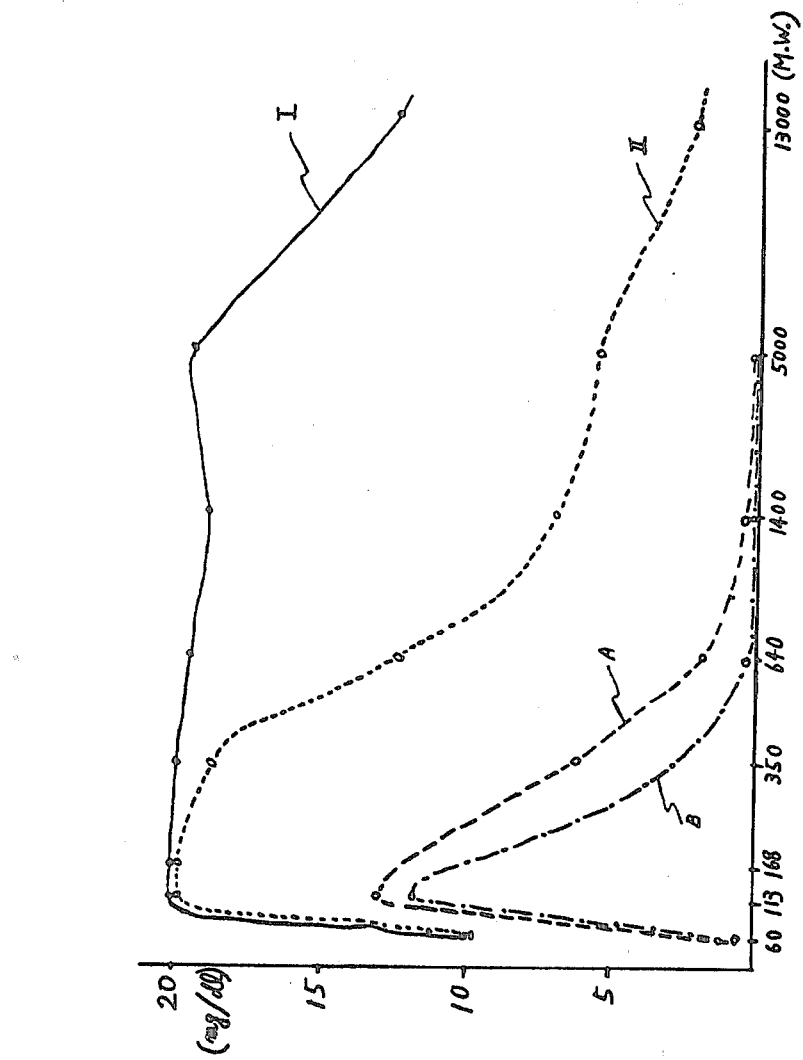

BLOOD PURIFICATION WITH COATED ACTIVATED CARBON SPHERES

This is a continuation of application Ser. No. 698,607, filed June 22, 1976, now abandoned.

This invention relates to a process of using coated beads-shaped activated carbon as an adsorbent for the purification of the blood.

It is popular to use means or apparatus for the purification of the blood, for treating the patients suffering from dysfunction of the kidney or the liver. There are two types of said means currently in use, i.e., a dialysis type which utilizes a dialysis diaphragm, and an adsorption type which utilizes absorbents. The dialysis type is more popularly used at the present time. However, this type has drawbacks in that the apparatus is so large that the operation is difficult, and a long time is required for the purification of the blood. Studies are therefore now progressing to develop adsorption type means wherein the above-mentioned drawbacks are excluded. However, such adsorption type has some drawbacks other than those in the dialysis type. The adsorbents used presently for the adsorption type are those which are prepared by coating crushed carbon originated from vegetables (hereinafter referred to as the coated crushed active carbon), for example, an active carbon made of carbonized shell of coconut (hereinafter referred to as the coated coconut active carbon). Coated crushed active carbon is prepared, for example, by dipping the original carbon into an ethyl alcohol-ethyl ether solution of pyroxylin, and drying the same. By electromicroscopic observation, a coated crushed active carbon, for example, the active carbon which is coated by the pyroxylin solution dissolved in the mixture of ethyl alcohol and ethyl ether, is not coated uniformly by pyroxylin film and has some uncoated area in which there are free carbon dusts exposed, because the crushed active carbon has an irregular form and numerous sharp edges and strict cleavage surfaces. The edge portions of such carbon are often broken off even by slight outer shock, resulting in formation of free carbon dusts. The carbon dusts may be taken into the blood when the blood is treated with such carbon, and finally deposited on the internal organs. The adsorbent is usually further covered with a film of albumin or the like over the above-mentioned coating in order to avoid adherence and coagulating of the blood components. When the crushed carbon is used, however, it is difficult to ensure this outer covering sufficiently. There is also often found that blood platelets and the like adhere to the carbon, due to large numbers of sharp projections and edges of the carbon. Consequently, a temporary reduction of the blood platelet cannot be avoided. There is also known an improved method, wherein coating of the coconut active carbon with pyroxylin is carried out by phase separation process using dioxan as a solvent. Although the method may provide a relatively better coating film and considerably reduced amount of free carbon dust, the reduced amount is not sufficient to permit practical use, and in addition, this method also has the drawback in that blood components adhere to the carbon. The greatest drawback of this method is that a large amount of harmful dioxan remains in the carbon as residual solvent due to the difficulty encountered in its removal, with the result that the dioxan necessarily dissolves into the blood.

Further, although the coated crushed carbon exhibits a relatively high adsorption capacity for the materials having low molecular weight, it does not show so high adsorption capacity for the materials having medium molecular weight.

The so called "kidney toxin" in the blood of a patient suffering from kidney failure, whose blood must be purified, comprises various materials having different molecular weights. The components of medium molecular weights having unknown chemical structure play a more important role, as compared with those of low molecular weights.

It is, therefore, an important drawback of the coated crushed active carbon that the adsorption capacity on the medium molecular weight materials is low.

There has also been known a granular active carbon which is prepared by mixing a powdery carbon with a binder, granulating the mixture, and carbonizing to activate the resulting granule. When such granular active carbon is coated, the resulting coated granular active carbon is superior to coated crushed carbon with regard to the free carbon dust, adherence of the blood and facility of coating, but the granular active carbon has very low adsorption capacity. This granular active carbon is, for the latter reason, unsuitable for use in the purification of the blood.

Under these circumstances, blood purification apparatus using the adsorption type means has not as yet been available.

The present inventors have paid particular attention to the beads-shaped activated carbon, and studied as to whether the said beads-shaped activated carbon coated by film can be employed as an adsorbent in a blood purification apparatus. We have found, consequently, that the beads-shaped activated carbon can be easily coated by a conventional method of coating without using the phase separation method of dioxan, and that the resulting coated beads-shaped activated carbon has superior properties compared to the prior adsorbents from the viewpoint of the strength, the free carbon dust, the ignited ash, the residual solvent and adherence of the blood. It was further observed that the carbon used in this invention shows high adsorption capacity for the materials having medium molecular weight.

An object of the present invention is therefore to provide a process of using a coated beads-shaped activated carbon for the purification of the blood, which is prepared by coating a beads-shaped activated carbon with a film-forming material.

The beads-shaped activated carbon to be used in the present invention is an active carbon having a nearly perfect sphere form, which is obtained from pitch as a source material through melt molding, that is, a process for the molding of melted material. The beads-shaped activated carbon is different from conventional crushed or granulated active carbon. More particularly, the beads-shaped activated carbon can be prepared by, for example, dispersing the pitch in melted state into water to form a sphere, making said sphere non-fusible and carbonizing the same. As for detailed descriptions of the preparation for the beads-shaped activated carbon, refer to Japanese Patent Publication Nos. 25117/74 and 18879/75, for example. Such beads-shaped activated carbon is available in the market under the name of beads-shaped activated carbon (BAC) [Trade Mark, manufactured and sold by Taiyokaken Kabushiki Kaisha in Japan].

The film-forming material is selected from the materials which may provide a semipermeable film. There may be mentioned pyroxylin, polypropylene, copolymer of vinyl chloride-vinylidene chloride, ethylene glycol polymethacrylate, colagen, and the like, for example.

A conventional process may be employed for coating the beads-shaped activated carbon with the film-forming materials. Examples of such processes include pan coating, air suspension coating, spray drying, and the like. As a solvent to be employed for dissolving the film-forming material in the coating process, it is desirable to use a solvent which can be easily removed at a drying step, and has a low toxicity even if the solvent is dissolved into the blood.

In view of this point, ethanol is an especially preferred solvent, when pyroxylin is used for the film-forming material.

When the coated beads-shaped activated carbon is used for the purification of the blood, it is desirable to further coat it with a film such as albumin or the like, on the surface of the film of the coated beads-shaped activated carbon as mentioned above, for preventing the adherence and coagulating of the blood.

The coated beads-shaped activated carbon used in the present invention shows less quantity of the free carbon dust, the ash to be dissolved out, the residual solvent, and adsorption and coagulation of the blood components, as well as high safety, compared with prior coated coconut active carbon. Moreover, said active carbon used in the present invention shows a high adsorption capacity for toxic ingredients in the blood, a high functionality, and a high facility of coating and operation, compared with the coconut active carbon and the granular active carbon.

The purification of blood can be thus carried out safely and effectively by using the coated beads-shaped activated carbon according to the present specification.

The attached drawing is a graph of an adsorption spectrum which illustrates the adsorption capacity of the coated beads-shaped activated carbon according to the present invention (I) (shown by solid line) compared with coated coconut active carbon (II) (shown by dotted line), coated granular active carbon (A) (shown by broken line) and a different coated granular active carbon (B) (shown by chain line).

This invention will be illustrated by the following examples and experiments.

Initially, however, the preparation of the beads-shaped activated carbon in accordance with the aforementioned publications will be described.

Thus, Japanese Patent Publication No. 25117/74 discloses a process for the preparation of formed active carbon, characterized by using as the starting material a pitch which has a carbon content of 90 to 97.0%, and an average molecular weight of more than about 400, provides a distance of crystal-faces less than 6.80 Å as subjected to heat treatment up to 2400° C. in an inert atmosphere, and can be modified by preliminary oxidation to increase said distance to over 6.94 Å. This process involves melt-forming the pitch, treating the thus formed pitch in a gas containing at least one or more oxidative gases selected from the group consisting of oxygen, ozone, nitrogen oxides, $SO_3$ and halogens, to introduce a functional group and to carry out an infusibilization treatment, and burning the infusible product in an inert or non-oxidative atmosphere. In Example 1 of this publication, a crude oil was injected into steam which was over-heated to about 2000° C., cracked at about 1200° C. for 0.002 second and quenched, to obtain a tarry product, which was then distilled to remove a fraction below 400° C. under ordinary pressure, thus producing a pitch. The carbon content in the pitch was 95.3% as determined by elemental analysis and the average molecular weight was about 800 as measured by the VPO method. This pitch was made into hollow spheres using a plasticizer and benzene as an expansion agent through a conventional process, comprising the steps of dispersing it in a liquid, drying to control the content of the benzene, expansion, and drying for removing the benzene. The spheres had a mean grain size of 250$\mu$ and a membrane thickness of 10$\mu$. 75 g (500 cc) of the hollow spheres were put in a rotary flask having a capacity of 1000 cc, and heated to 130° C. in an oil bath. An oxidative gas comprising air containing 5% by volume of $NO_2$ was introduced into the flask at a flow rate of 2000 cc/min. and the temperature of the oil bath was elevated at a rate of 100° C./h. When the temperature of the oil bath reached 350° C., the introduction of said oxidative gas was stopped. The hollow spheres were then cooled to room temperature. The weight of the hollow spheres was increased to 82.5 g after these treatments. This shows that the spheres were sufficiently oxidized, and completely converted into infusible bodies. These infusible hollow sphere bodies were heated to 850° C. at a rate of 15° C./min. in a stream of nitrogen at a rate of 1000 cc/min., and held at said temperature for 60 minutes to carbonize them. There were thus obtained 58 g. of the active carbon in the form of hollow spheres having excellent activity.

Japanese Patent Publication No. 18879/75 discloses a process for the preparation of spherical activated carbon, characterized in that a pitch having a softening point of 50° to 350° C., a carbon content of 80 to 97%, an atomic ratio of hydrogen/carbon from 0.2 to 2.5, and a content of insolubles in nitrobenzene from 0 to 50%, is admixed homogeneously with or without an organic solvent miscible with the pitch, the pitch or the pitch-organic solvent mixture is subjected to melt-dispersion by using, as a dispersing medium, water containing a suspension agent under atmospheric or super-atmospheric pressure at a temperature of 50° to 300° C., the resulting spherical pitch bodies are, if necessary, freed from the solvent, and an infusiblization and carbonization treatment are carried out. In Example 1 of this publication, a crude oil was injected into steam heated to 2000° C., cracked during a contacting period of time for 0.005 second, and quenched, to obtain a tarry product. This product was distilled to remove a fraction below 430° C. under atmospheric pressure to produce a pitch. The pitch had a softening point of 205° C., insoluble content of 32% in nitrobenzene, carbon content of 95% and a H/C ratio of 0.56. 90 Kg of the pitch and 30 Kg of benzene were charged into an autoclave having a capacity of 300 ml equipped with wings for stirring. The mixture was heated to 170° C. to melt it. To the mixture, there were added 230 Kg of aqueous 0.3% polyvinylalcohol solution, as a suspension agent. This mixture was stirred at 150° C. for 40 minutes at 360 rpm, dispersed, quenched and dehydrated centrifugally. The product was heated in a fluid bed to remove benzene therefrom. Spherical pitch bodies having a mean size of 300$\mu$ were thus obtained. The spherical pitch bodies were sufficiently infusiblized by elevating the temperature, starting from 200° C., at the rate of 25° C./hr in a multiple fluid bed with introduction of heated air, and retained at 300° C. for two hours with continuous introduction of heated air. Thereafter, the spherical pitch bodies were heated at 1000° C. in a nitrogen atmosphere for one hour to carbonize them. The spherical carbons produced had a mean size of 280μ and exhibited a powdering amount of less than 0.005% by weight.

EXAMPLE 1

To 5 g of pyroxylin were added 200 ml of absolute ethanol, and the mixture was blended with homogenizer to be micronized. Thereafter, 800 ml of absolute ethanol were added to the solution. The solution was sufficiently mixed and allowed to stand for 24 hours to make a 0.5% solution for spray.

There were placed 500 g of beads-shaped activated carbon (BAC) having an average diameter of 0.6 mm, into a coating pan having a depth of 25 cm, an outside diameter of 30 cm, and a bore of 17 cm. The active carbon was coated by spraying 500 ml of said solution while blowing with rotation. The coated active carbon was then dried at 80° C. for two days, to obtain the coated beads-shaped activated carbon.

The resulting coated beads-shaped activated carbon was dipped in water to debubble under a reduced pressure, and sterilized by steam under pressure. The sterilized material was then charged into a vessel of plastics for the purification of the blood, the vessel having diameter of 3 cm, height of 7 cm, and volume of 50 ml and equipped with two filters at upper end and lower end thereof respectively. The vessel was charged with physiological saline water, which was then replaced with 80 ml. of 0.5% physiological saline solution of albumin. After standing overnight, the active carbon was washed by a flow of physiological saline water. The blood was passed through this vessel to purify the blood.

EXAMPLE 2

The same procedure was repeated, except that ethylene glycol polymethacrylate (sold under Trade Mark "HYDRON") is substituted for pyroxylin.

EXPERIMENT

The coated beads-shaped activated carbon obtained by Example 1 was subjected to tests to determine its properties.

The coated coconut active carbon used for the control in this experiment is prepared by coating coconut active carbon available in the market with pyroxylin according to the phase separation process. The coated granular active carbons (A) and (B) were respectively prepared by coating two granular active carbons (A) and (B) selected from those which are available in the market and offered by different manufacturers, with pyroxylin according to the same method as in the preceding Example 1.

(1) Amount of free carbon dust

Ten grams of coated beads-shaped activated carbon were charged into a 200 ml conical flask. There was added into the flask physiological saline water which previously filtered twice by a millipore filter of 0.45μ. The contents were degassed under a reduced pressure, and decanted to remove excess water. Additional 150 ml of filtered physiological saline water were charged, and the mixture was shaken for 45 minutes at 130 rpm in an incubator. After the shaking, the number of the free carbon dust particles having sizes more than 1.2 micron was determined by a coolter counter. Conventional coated crushed coconut active carbon was selected for the control.

The result is shown in the following.

|  | Number of free carbon dust particles per ml |
|---|---|
| Coated beads-shaped activated carbon | 0–200 |
| Coated crushed coconut active carbon | 3000–5000 |

(2) Adsorption capacity 2 grams of the coated beads-shaped activated carbon were placed in several vessels. There were added to each vessel 200 ml of physiological phosphoric acid buffer solution containing 20 mg/ml of materials having various molecular weights respectively, and the respective mixtures were shaken at 115 rpm for 2 hours in an incubator. Thereafter, each adsorption capacity was determined. The coated crushed coconut active carbon and the coated granular active carbons (A) and (B) were selected for the controls. The results of the determination are recorded on the graphical drawing, with molecular weight on horizontal axis and adsorbed concentration (mg/dl) on vertical axis. As clearly shown in the graph, the coated beads-shaped activated carbon according to present invention has a high adsorption capacity not only on the materials having low molecular weight, but also on the materials having medium molecular weight. On the other hand, the coated crushed coconut active carbon shows a considerable high adsorption capacity for the former materials, but does not show this capacity for the latter materials. The coated granular active carbons (A) and (B) exhibit low adsorption capacity on the former materials, and scarcely any adsorption capacity on the latter material.

In the kidney toxin present in the patient suffering from kidney failure, the substances having medium molecular weight with unknown chemical structure play the essential part, rather than the substances having a relatively low molecular weight, such as urea, creatine, uric acid, and the like. It is considered that the remarkable nervous lesion is mainly caused by substances having medium molecular weight. Therefore, it is a substantial merit of the coated beads-shaped activated carbon according to the present invention that said active carbon exhibits high adsorption capacity for the materials having medium molecular weight, in the purification of the blood.

(3) Adherence of components of the blood 10 g of each of a coated beads-shaped activated carbon and another coated beads-shaped activated carbon which is further covered with albumin were charged into columns, respectively. Through these columns, 25 ml of the blood were passed at a velocity of 25 ml/min. The same operation was repeated 25 times. 100 ml of physiological saline water were passed through each column, followed by 100 ml of distilled water. The respective active carbons were taken out from the columns, and lyophilized. The degree of adherence of components of the blood to the carbons was inspected by observing the surface of the carbons with an electronic microscope. Further, both the coated crushed coconut active carbon and the other coated crushed coconut active carbon which is further covered with albumin were selected for the controls.

|  | Sticking of the blood platelet | Sticking of the blood corpuscle |
| --- | --- | --- |
| Coated beads-shaped activated carbon | ± | − |
| Ditto, but further coated with albumin | − | − |
| Coated crushed coconut active carbon | + + | + |
| Ditto, but further coated with albumin | − | − |

In this table, − represents no adherence, ± represents slight adherence, + represents considerable adherence, and + + represents adherence to an extent that most of surface of the carbon is covered.

(4) Residual solvent

Only an amount of from about 150 to about 200 ppm of ethanol remained in the coated beads-shaped activated carbon of the preceding Example 1. The ethanol could not be detected in the blood, after the blood was treated by this coated beads-shaped activated carbon. On the other hand, in the case of the coated crushed coconut active carbon which is prepared by phase separation method using dioxan as a solvent, the residual dioxan amounted to as large as about 50,000 ppm, notwithstanding severe treatment for removing the dioxan, for example, by vacuum-drying or lyophilization. About 20,000 ppm of the dioxan remains, even if the active carbon has been dried at a high temperature ranging from 80° C. to 120° C. for 10 days. This dioxan will be released gradually into the blood, when the blood is treated with such a coated crushed coconut active carbon.

(5) Priming volume

The larger the volume of priming, the larger is the amount of the blood which is recycled out of the body; and the risk of failure is increased accordingly. The priming volume may become as small as from about 60 to 110 ml, when the coated beads-shaped activated carbon according to the present invention is used for the adsorbent, while the amount is about 400 ml when the conventional dialysis type of artificial kidney is used.

We claim:

1. A method of purifying blood which comprises passing the blood through a mixture of beads-shaped activated carbon coated with a semi-permeable film-forming material selected from the group consisting of pyroxylin, polypropylene, vinyl chloride-vinylidene chloride copolymer, ethylene glycol polymethacrylate and colagen, wherein the beads-shaped activated carbon is prepared by dispersing molten pitch into water to form spheres, rendering said spheres infusible, and carbonizing said infusible spheres.

2. A method according to claim 1, wherein the beads-shaped activated carbon is prepared by dispersing molten pitch into water to form spheres, treating the spheres in a gas containing at least one oxidative gas selected from the group consisting of oxygen, ozone, a nitrogen oxide, $SO_3$ and a halogen to render the spheres infusible, and carbonizing the infusible spheres in an inert or non-oxidative atmosphere, said pitch starting material having a carbon content of 90 to 97%, an average molecular weight of greater than about 400, a distance of crystal-faces less than 6.80 Å when subjected to heat treatment up to 2400° C. in an inert atmosphere, said distance being increased to over 6.94 Å when, prior to said heat treatment, said pitch is preliminarily oxidized and then subjected to said heat treatment.

3. A method according to claim 1, wherein the beads-shaped activated carbon is prepared by homogeneously mixing pitch with an organic solvent miscible with the pitch, melting the mixture, adding a mixture of water and a suspension agent to the molten mixture, stirring the resultant mixture at 50° to 300° C., removing the solvent from the stirred mixture, and subjecting the thus obtained spherical pitch bodies to infusibilization and carbonization, said pitch starting material having a softening point of 50° to 350° C., a carbon content of 80 to 97%, a hydrogen/carbon atomic ratio of from 0.2 to 2.5 and a nitrobenzene-insoluble content of from 0 to 50%.

4. A method according to claim 1, wherein the film-forming material is pyroxylin.

5. A method according to claim 1, wherein a coating of albumin is further applied to the surface of the film of the coated beads-shaped activated carbon.

* * * * *